US011918361B2

(12) United States Patent
Ager

(10) Patent No.: US 11,918,361 B2
(45) Date of Patent: Mar. 5, 2024

(54) APPARATUS FOR MEASURING ISOMETRIC MUSCLE STRENGTH

(71) Applicant: FORCE HOOKS PTY LTD, Padbury (AU)

(72) Inventor: Jason Christopher John Ager, Hillarys (AU)

(73) Assignee: Force Hooks Pty Ltd, Padbury (AU)

( * ) Notice: Subject to any disclaimer, the term of this patent is extended or adjusted under 35 U.S.C. 154(b) by 434 days.

(21) Appl. No.: 17/292,427

(22) PCT Filed: Nov. 7, 2019

(86) PCT No.: PCT/IB2019/059589
§ 371 (c)(1),
(2) Date: May 7, 2021

(87) PCT Pub. No.: WO2020/095251
PCT Pub. Date: May 14, 2020

(65) Prior Publication Data
US 2022/0007979 A1 Jan. 13, 2022

(30) Foreign Application Priority Data
Nov. 7, 2018 (AU) .................. 2018904245

(51) Int. Cl.
*A61B 5/22* (2006.01)
*A61B 5/00* (2006.01)
*G01L 1/22* (2006.01)

(52) U.S. Cl.
CPC ............ *A61B 5/224* (2013.01); *A61B 5/6895* (2013.01); *A61B 5/742* (2013.01); *G01L 1/22* (2013.01); *A61B 2562/0261* (2013.01)

(58) Field of Classification Search
CPC ....... A61B 5/224; A61B 5/6895; A61B 5/742; A61B 2562/0261; A61B 5/22; G01L 1/22; A63B 21/078; A63B 21/0023
See application file for complete search history.

(56) References Cited

U.S. PATENT DOCUMENTS

| 4,939,933 A * | 7/1990 | Curran | A61B 5/103 |
| | | | 482/901 |
| 2012/0137771 A1* | 6/2012 | Cyphery | A61B 5/224 |
| | | | 73/379.02 |
| 2017/0100624 A1* | 4/2017 | Young | A63B 17/04 |

\* cited by examiner

*Primary Examiner* — Xin Y Zhong
(74) *Attorney, Agent, or Firm* — Brown & Brown IP Law PLLC

(57) ABSTRACT

An apparatus for measuring isometric muscle strength and dynamic strength when a limb is fixed, wherein the apparatus comprises: an attachment assembly for releasably attaching the apparatus to a support frame of an item of exercise equipment; a strain gauge configured to measure compressive or tensional forces; and a connection assembly for releasably connecting the strain gauge to a moveable component (e.g. barbell) of the exercise equipment wherein when connected makes the component immoveable such that forces exerted on the formerly moveable component require isometric muscle contraction or dynamic contraction while the limb is fixed that can be measured by the strain gauge.

23 Claims, 13 Drawing Sheets

APPARATUS FOR MEASURING ISOMETRIC MUSCLE STRENGTH

FIELD

The present invention relates to the measurement of muscle strength and, more particularly, an apparatus for measuring isometric muscle strength and dynamic strength when a limb is fixed.

BACKGROUND

Isometric exercises, or isometrics, are types of strength training that involve the static contraction of muscles without any visible movement in joint angles or muscle length. Isometrics are carried out in static positions, rather than dynamic actions that involve a range of motion. For example, a simple isometric exercise may involve a person lifting a barbell bar that is immovably attached to the supporting frame of a weight rack. Another example may involve a person pulling on a strap tied to one of their limbs that is immovably attached to a post or supporting frame.

Isometric exercises are beneficial because they minimize stress placed on joints and are, therefore, ideal for rehabilitation purposes. Isometric exercises are particularly beneficial for persons with injuries to ball-and-socket joints, such as the knee, hip or shoulder, and can also help improve bone density and reduce the risk of osteoporosis. Isometric exercises can also be carried out by persons suffering from arthritis which can be aggravated by using muscles that move a joint through the full range of motion.

The ability to measure a person's isometric strength and dynamic strength when a limb is fixed is beneficial in many situations including in sports training, physiotherapy and rehabilitation. Isometric strength is currently measured using elaborate assemblies and systems that are custom made and comprise a large number of parts. These systems are expensive to manufacture and the scope of physical activities that can be performed and assessed using them is limited as they are generally designed to evaluate isometric muscle contractions and dynamic strength when a limb is fixed for specific exercises only.

In this context, there is a need for improved ways for measuring isometric muscle strength.

SUMMARY

According to the present invention, there is provided an apparatus for measuring isometric muscle strength and dynamic strength when a limb is fixed, wherein the apparatus comprises: an attachment assembly for releasably attaching the apparatus to a support frame of an item of exercise equipment; a strain gauge configured to measure compressive or tensional forces; and a connection assembly for releasably connecting the strain gauge to a moveable component (e.g. barbell) of the exercise equipment wherein when connected makes the component immoveable such that forces exerted on the formerly moveable component require isometric muscle contraction or dynamic contraction while the limb is fixed that can be measured by the strain gauge.

The connection assembly may comprise first and second clamping members that are pivotable relative to one another for releasably clamping part of the strain gauge to the moveable component of the exercise equipment.

The first clamping member may be attached to an end of the strain gauge and the second clamping member may be pivotally attached to the first clamping member.

The connection assembly may further comprise a latch for fastening the clamping members together when clamped around the moveable component.

The latch may comprise:
a tab member connected to the first clamping member; and
a slot formed in the second clamping member for receiving the tab member, wherein an end of the tab member comprises a flange for releasably securing the tab member in the slot when the clamping members are fastened together.

The clamping members may be configured to engage an elongate bar of a barbell rack.

Each of the clamping members may comprise a curved innermost surface for engaging a curved outermost surface of the elongate bar.

The clamping members may be releasably attached to the apparatus such that they may be removed and replaced with an alternative connection assembly.

The apparatus may further comprise a receptacle and the attachment assembly and strain gauge may each be connected to the receptacle.

The lowermost end of the strain gauge may be attachable to the receptacle and an uppermost end of the strain gauge may be attached to the connection assembly.

The lowermost end of the strain gauge may be pivotally attached to the receptacle such that the strain gauge may pivot relative to the receptacle in response to the moveable component of the exercise equipment being moved.

The attachment assembly may comprise an elongate peg that extends outwardly from the receptacle and is insertable into a hole of the support frame of the exercise equipment.

The attachment assembly may comprise a locking system for locking the elongate peg in the hole of the support frame once inserted therein.

The locking system may comprise at least one aperture formed in the elongate peg that is configured to receive a locking pin for locking the elongate peg in the hole of the support frame when inserted therein.

The locking system may comprise a plurality of apertures formed in the elongate peg for receiving the locking pin.

The apparatus may further comprises a rectangular control housing disposed between the strain gauge and the receptacle, wherein the control housing contains a processor and power source for operating the strain gauge.

The strain gauge may comprise a load cell configured such that an electrical resistance of the load cell changes in response to compressive or tensional forces exerted on the load cell.

The load cell may comprise an s-type load cell.

The apparatus may further comprise a communications port for connecting a peripheral device to the apparatus by wire for reading data measured using the strain gauge.

The apparatus may further comprise a radio transmitter for wirelessly reading data measured using the strain gauge using a peripheral device.

The connection assembly may comprise an aperture configured to receive a strap member for connecting the strain gauge to a moveable component of the exercise equipment that may be pulled by a user.

The receptacle, attachment assembly and connection assembly may each be made of steel, aluminum, carbon fiber or high strength composite materials.

The present invention also provides a system for measuring isometric muscle strength and dynamic strength when a limb is fixed that comprises a plurality of apparatuses, wherein each of the apparatuses is as described above and is attached to a support frame of an item of exercise equipment.

The item of exercise equipment may comprise a barbell rack and the system may comprise a pair of the apparatuses each attached to a support frame of the barbell rack.

BRIEF DESCRIPTION OF DRAWINGS

Embodiments of the invention will now be described by way of example only with reference to the accompanying drawings, in which.

DESCRIPTION OF EMBODIMENTS

Figure 1A:
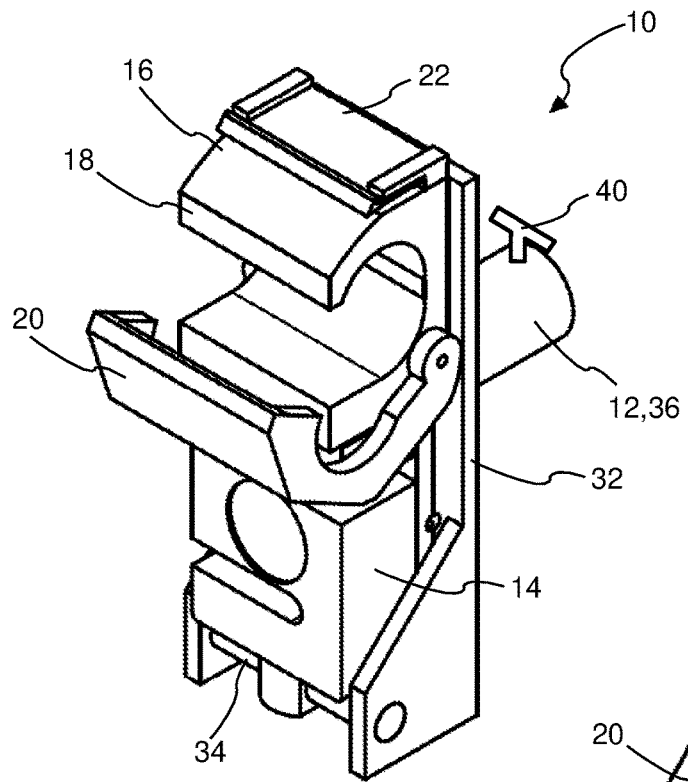
FIG. 1(a) is an isometric view of an apparatus for measuring isometric muscle strength according to an example embodiment of the invention, wherein the clamping members of the apparatus are shown in an open configuration.
Figure 1B:
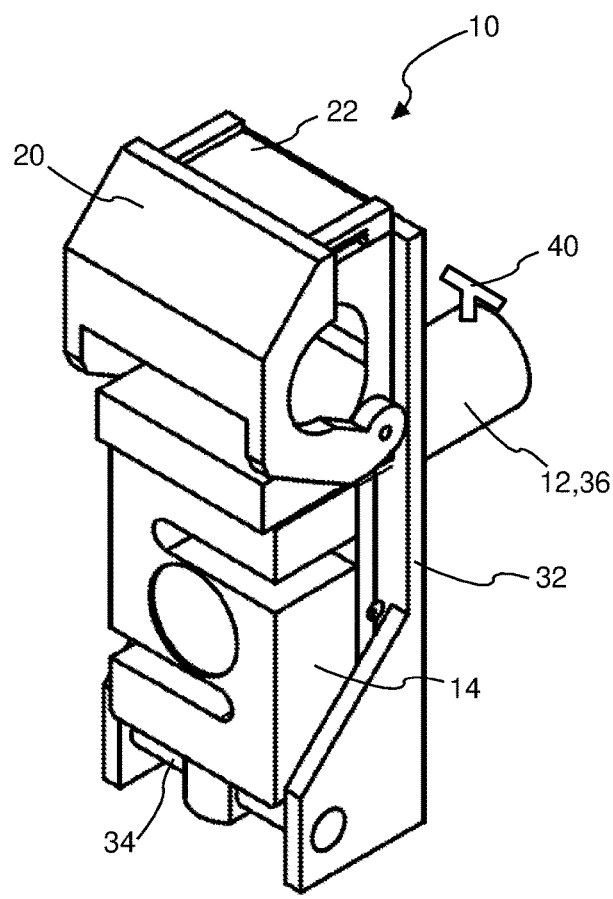
FIG. 1(b) is an isometric view of the apparatus of FIG. 1(a), wherein the clamping members are shown in a closed configuration.

Referring to FIGS. 1 to 13, example embodiments of the present invention provides an apparatus for measuring isometric muscle strength 10. The apparatus 10 comprises an attachment assembly 12 for releasably attaching the apparatus 10 to a support frame of an item of exercise equipment and a strain gauge 14 that is configured to measure compressive or tensional forces. The apparatus 10 further comprises a connection assembly 16 for releasably connecting the strain gauge 14 to a moveable component of the exercise equipment such that forces exerted on the moveable component by isometric muscle contraction are detected and measured by the strain gauge 14.

More particularly, the connection assembly 16 may comprise first and second clamping members 18,20 that are connected to part of the strain gauge 14. In the example depicted, the clamping members 18,20 are connected to a topmost part of the strain gauge 14. The clamping members 18,20 may be pivotable relative to one another such that they may be clamped around and to a moveable component of the exercise equipment and provide a secure and releasable connection. For example, the clamping members 18,20 may be clamped around an elongate bar of a barbell rack to releasably connect the strain gauge 14 to the bar.

The first clamping member 18 may be attached to the strain gauge 14 and the second clamping member 20 may be pivotally attached to the first clamping member 18. For example, the first clamping member 18 may be attached to a topmost end of the strain gauge 14 using a suitable attachment means such as a threaded bolt, screw, welded join or pin assembly.

Figure 2A:
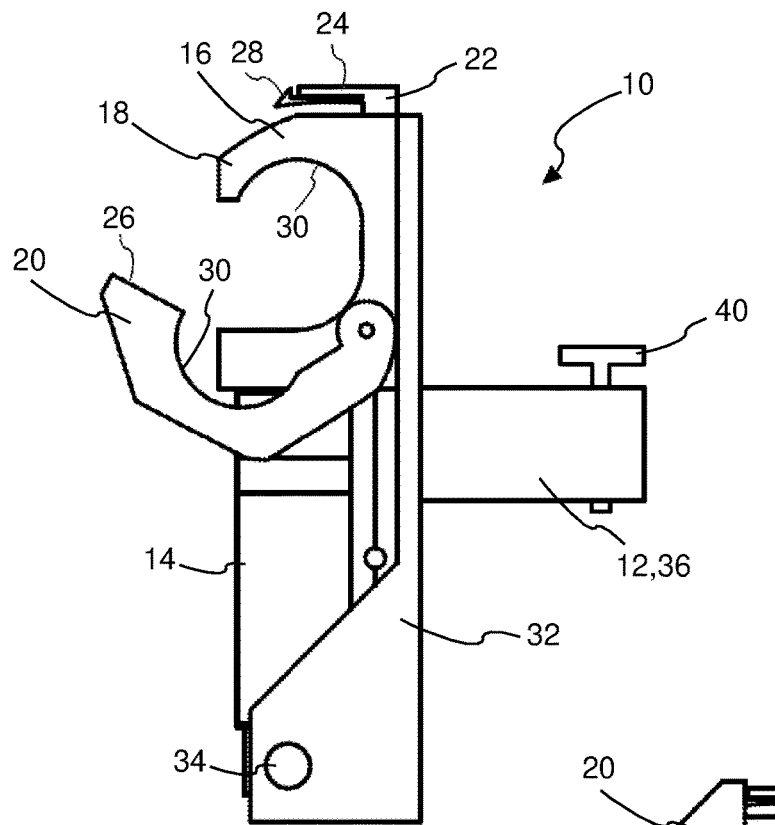
FIG. 2(a) is a side view of the apparatus of FIG. 1(a), wherein the clamping members are shown in an open configuration.
Figure 2B:
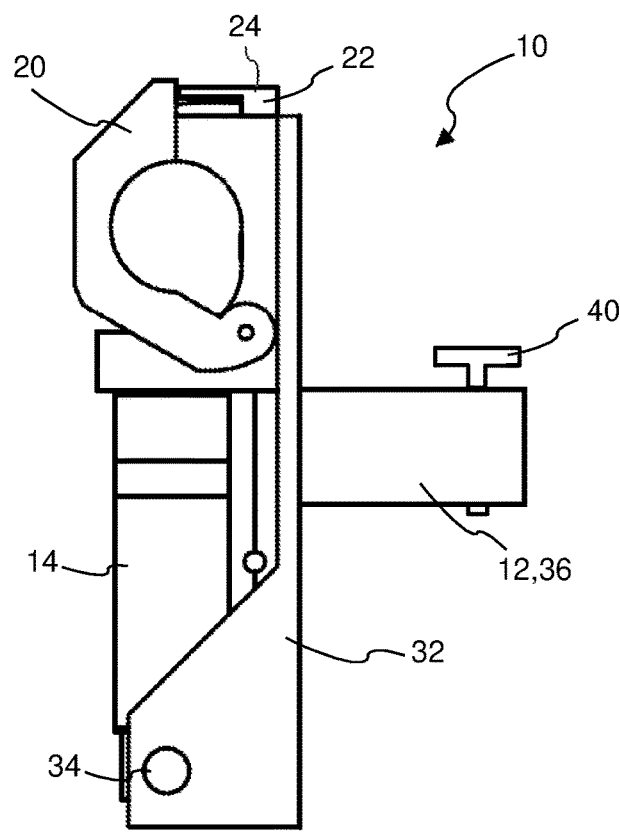
FIG. 2(b) is a side view of the apparatus of FIG. 1(a), wherein the clamping members are shown in a closed configuration.
Figure 3A:
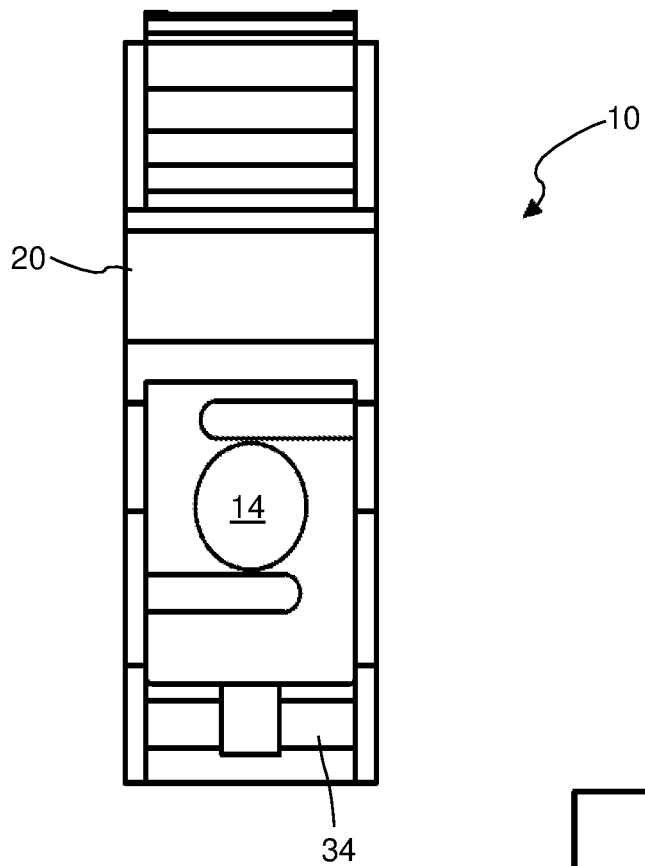
FIG. 3(a) is a front view of the apparatus of FIG. 1(a), wherein the clamping members are in an open configuration.
Figure 3B:
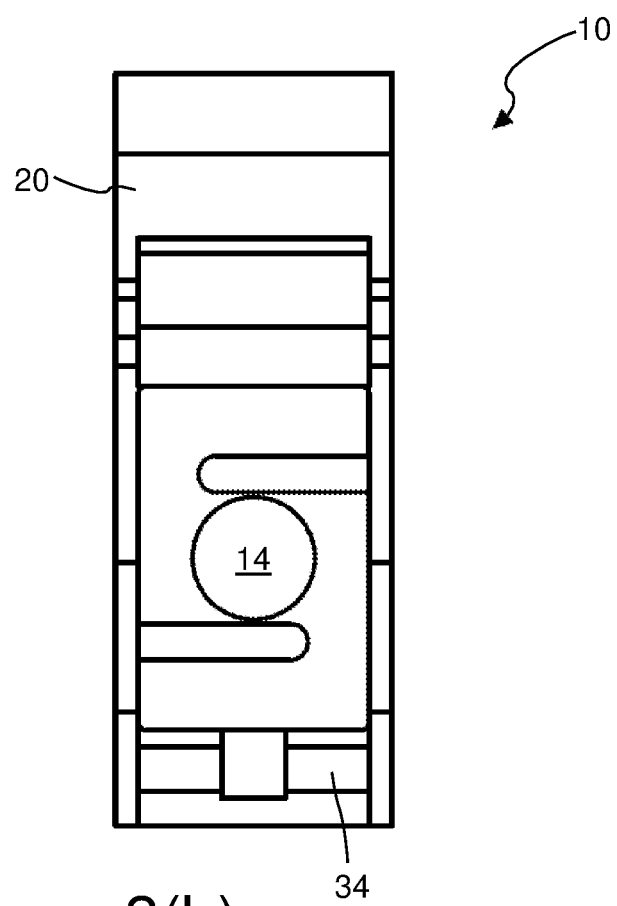
FIG. 3(b) is a front view of the apparatus of FIG. 1(a), wherein the clamping members are in a closed configuration.

The connection assembly 16 may further comprise a latch 22 for fastening the clamping members 18,20 securely together when they have been clamped to and around the relevant moveable component of the exercise equipment. As best shown in FIG. 2(a), the latch 22 may comprise a tab member 24 that is connected to a topmost surface of the first clamping member 18 and a slot 26 that is formed in the second clamping member 20. The slot 26 may be elongated and extend laterally across a surface of the second clamping member 20 that faces the first clamping member 18 such that the slot 26 receives the tab member 24 when the clamping members 18,20 are pushed together. An end of the tab member 24 may comprise a barbed flange 28 that releasably secures the tab member 24 inside of the slot 26 by interference fit when the clamping members 18,20 are fastened together.

In the example depicted in FIGS. 1 to 5 and 9 to 13 the clamping members 18, 20 are adapted such that they may be clamped onto an elongate bar of a barbell rack. Each of the clamping members 18, 20, therefore, comprise a curved innermost surface 30 for engaging a curved outermost surface of the elongate bar when the clamping members 18,20 are clamped around the bar.

The apparatus 10 may further comprise a receptacle 32 that the attachment assembly 12 and the strain gauge 14 are each connected to. As shown in the Figures, a lowermost end of the strain gauge 14 may be attached to a lower part of the receptacle 32 and an uppermost end of the strain gauge 14 may, in turn, be attached to the connection assembly 16.

The lowermost end of the strain gauge 14 may be attached pivotally to the lower part of the receptacle 32 via a pin 34. The pin 34 extends laterally across the apparatus 10 and may engage with a pair of complementary apertures formed in side walls of the receptacle 32. Referring also to FIGS. 9(a)-(b), this configuration allows the strain gauge 14 to be pivoted relative to the receptacle 32 about the axis formed by the pin 34 when the moveable component of the exercise equipment is moved during use.

The attachment assembly 12 may comprise a peg 36 that extends outwardly from a rearmost side of the receptacle 32. The peg 36 is configured such that it can be inserted into a hole of the support frame of the exercise equipment for releasably attaching the receptacle 32 to the support frame.

The attachment assembly 12 may further comprise a locking system for locking the elongate peg 36 in the hole of the support frame once inserted therein. The locking system may, for example, comprise at least one aperture 38 formed in the elongate peg 36 that is configured to receive a locking pin 40 for locking the elongate peg 36 in the hole of the support frame when inserted therein. The locking system may comprise a plurality of apertures 38 formed in the elongate peg 36 for receiving the locking pin 40 which advantageously allows the elongate peg 36 to be slotted and locked into support frame members that have a variety of different widths. In other examples, the locking system may be implemented using alternative locking assemblies such as threaded nuts and bolts 67 or an adaptor 68 for manufacturer specific designs.

The strain gauge 14 may comprise a load cell configured such that an electrical resistance of the load cell changes in response to compressive or tensional forces exerted on the load cell. In the example depicted, the strain gauge 14 comprises an s-type load cell.

Figure 4:
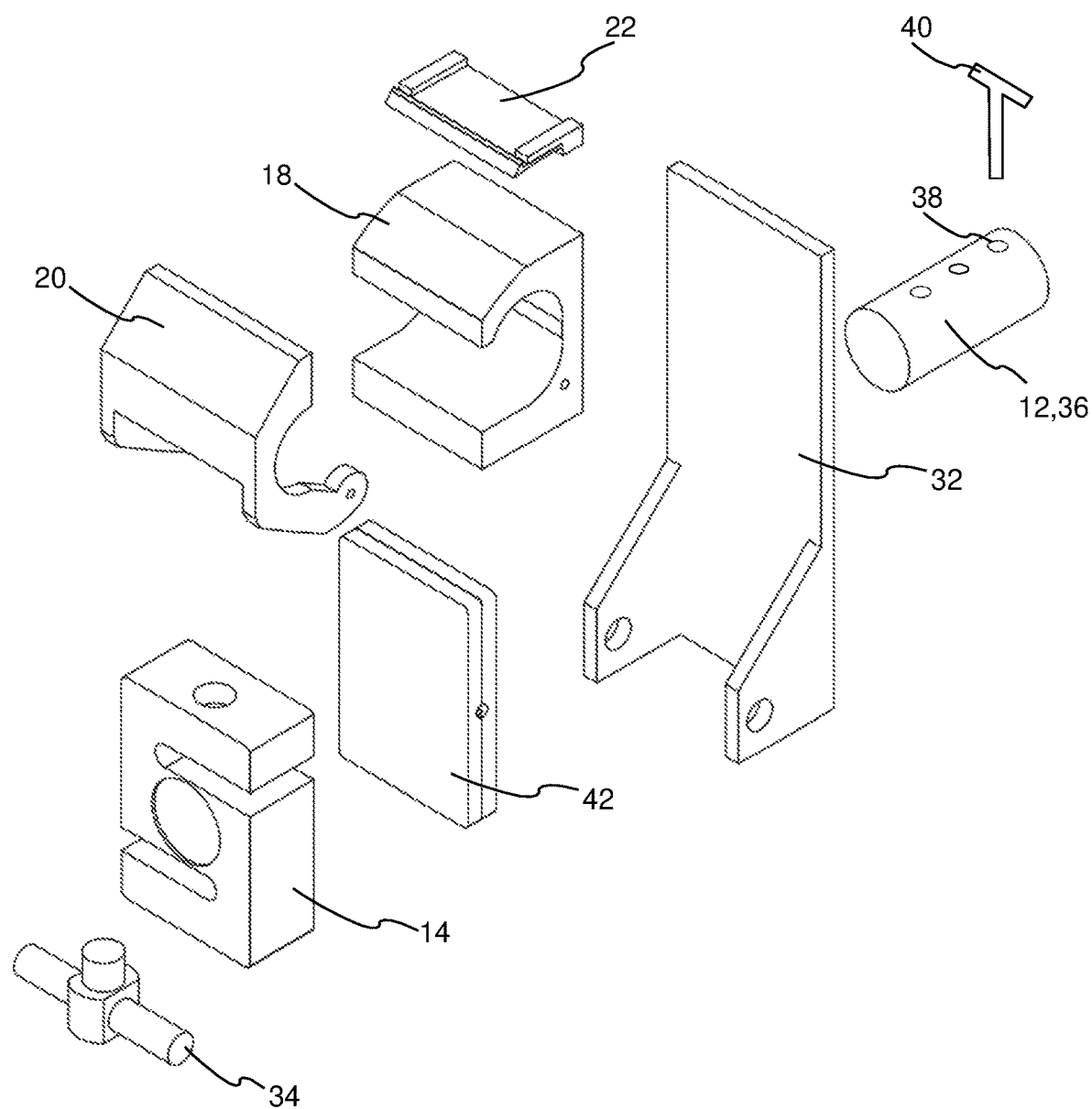
FIG. 4 is an exploded view of the apparatus of FIG. 1(a)

As best shown in FIG. 4, the apparatus 10 may further comprise a rectangular control housing 42 that is disposed between the strain gauge 14 and the receptacle 32. The control housing 42 may contain a processor and a power source 69, which is disposed between the strain gauge 14 and the receptacle 32, for operating the strain gauge 14.

In one example, the apparatus 10 may further comprise a communications port (not shown) on the control housing 42 for connecting a peripheral device to the apparatus 10 by wire for reading data measured using the strain gauge 14. In another example, the apparatus 10 may further comprises a radio transmitter on or within the control housing 42 that allows data measured using the strain gauge 14 to be accessed and read wirelessly using a peripheral device. The radio transmitter 65 may comprise an electronic device capable of transmitting data measured by the strain gauge 14 wirelessly such as, for example, a Bluetooth and/or WiFi transmitter.

The receptacle 32, attachment assembly 12 and connection assembly 16 may each be made of a strong, resilient material such as steel.

Figure 5:
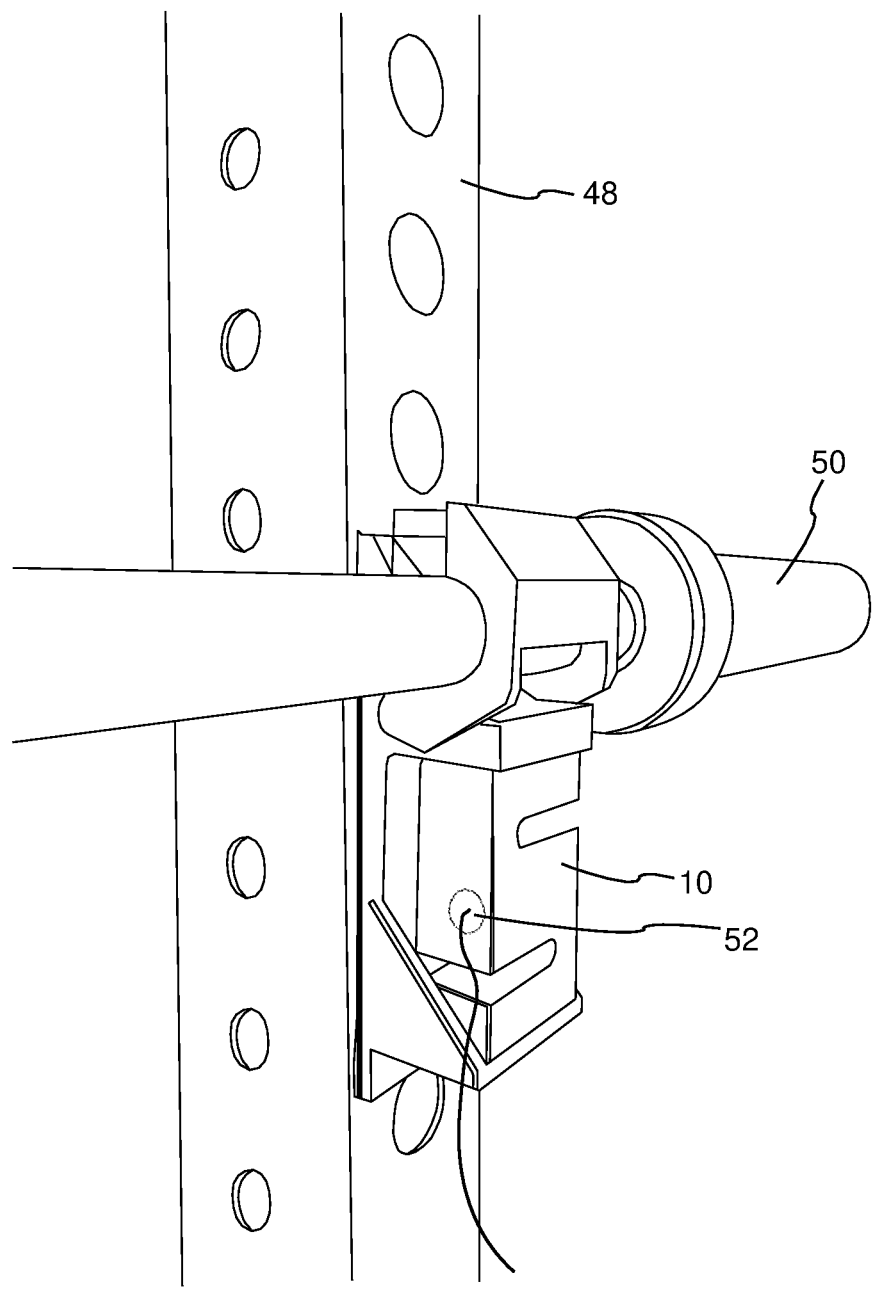
FIG. 5 is an isometric view of the apparatus of FIG. 1(a) attached to a support frame of a barbell rack.
Figure 6A:
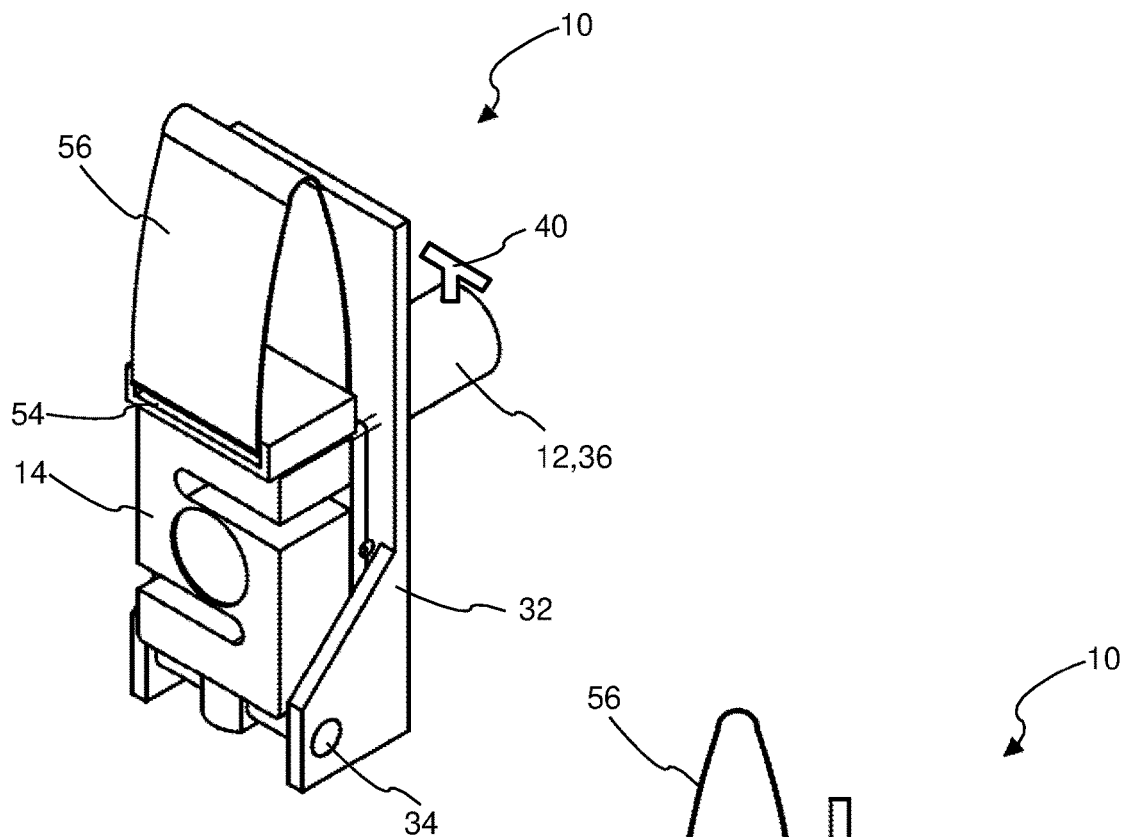
FIG. 6(a) is an isometric view of an apparatus for measuring isometric muscle strength according to a further example embodiment of the invention.
Figure 6B:
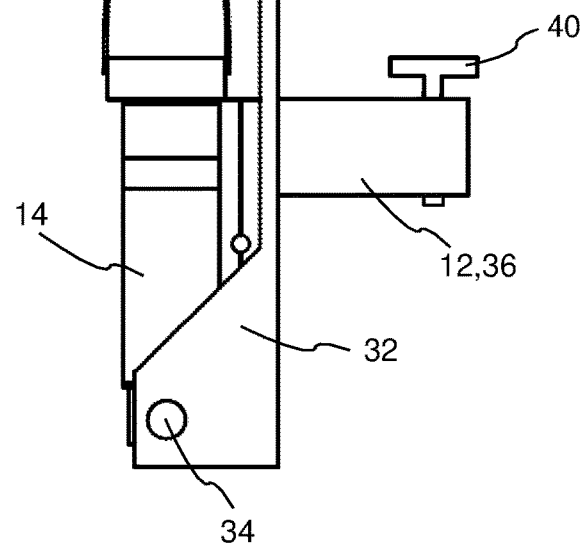
FIG. 6(b) is a side view of the apparatus of FIG. 6(a)
Figure 7:
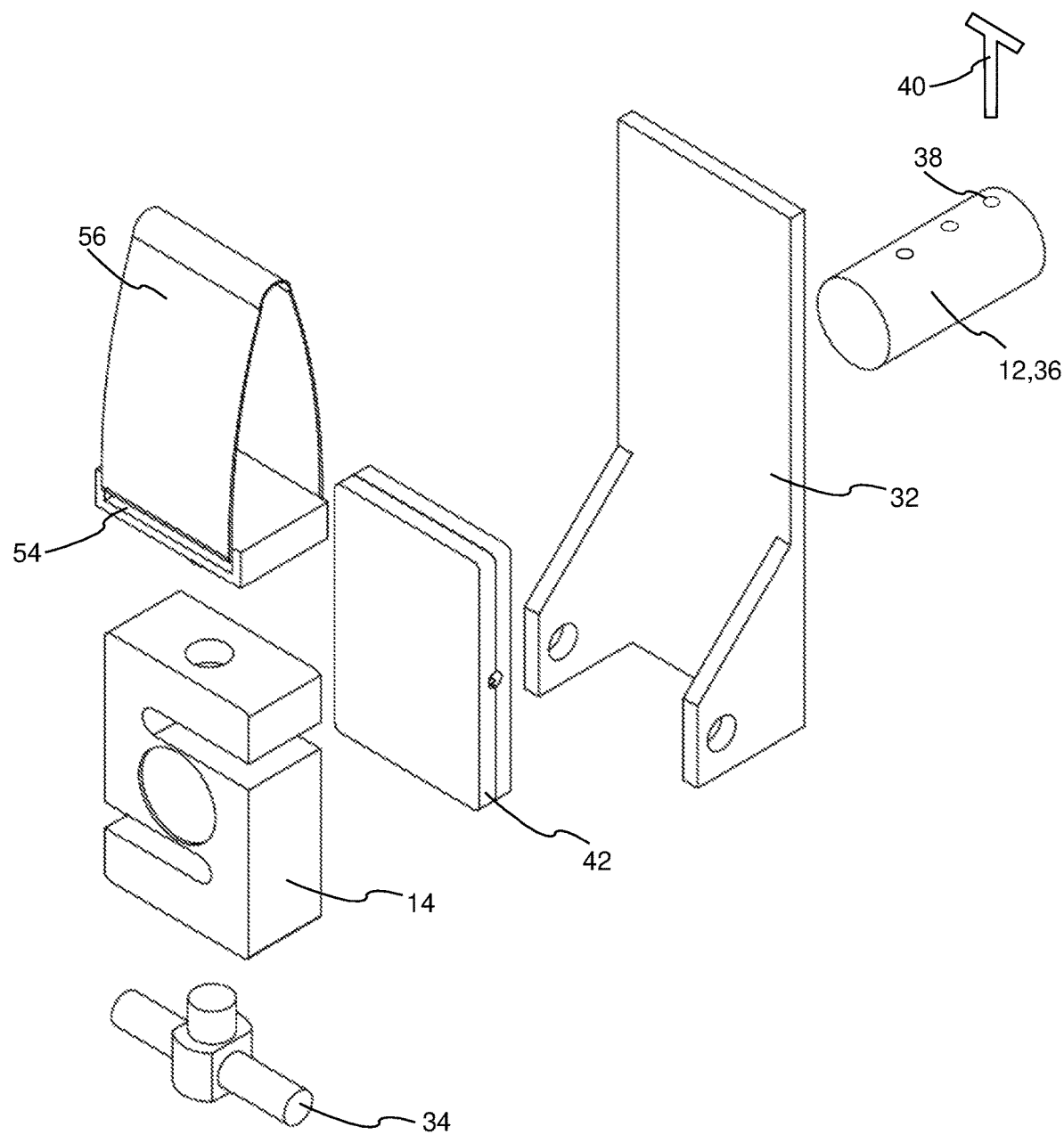
FIG. 7 is an exploded view of the apparatus of FIG. 6(a)
Figure 8:
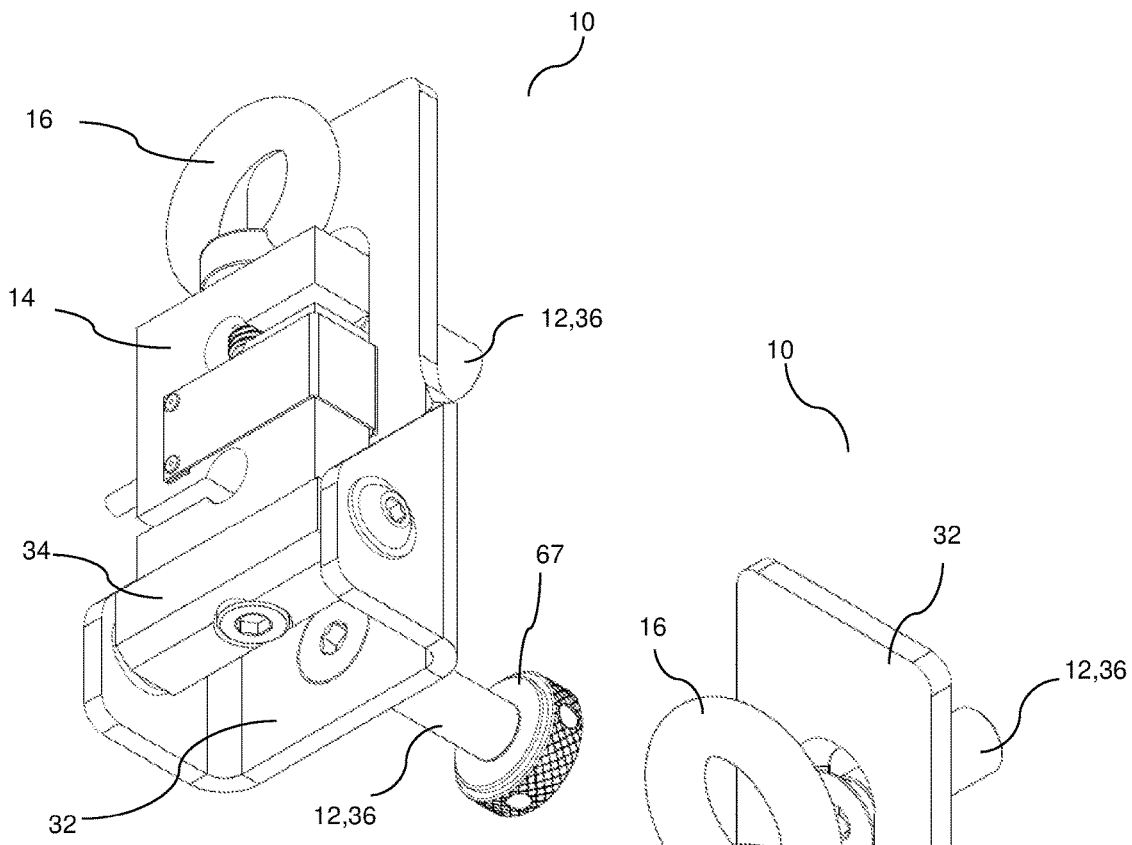
FIG. 8(a) is an isometric view of another embodiment of an apparatus for measuring isometric muscle strength wherein the connection assembly is an eye-bolt.
FIG. 8(b) is an elevated isometric view of the apparatus for measuring isometric muscle strength of FIG. 8(a)
Figure 8:
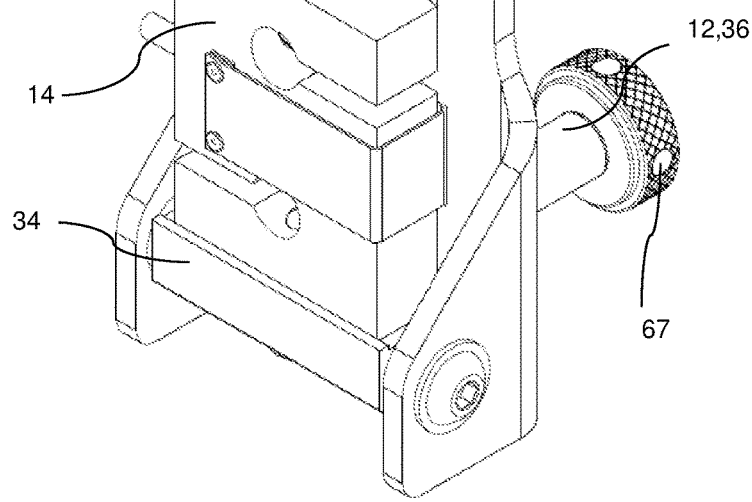
Figure 9:
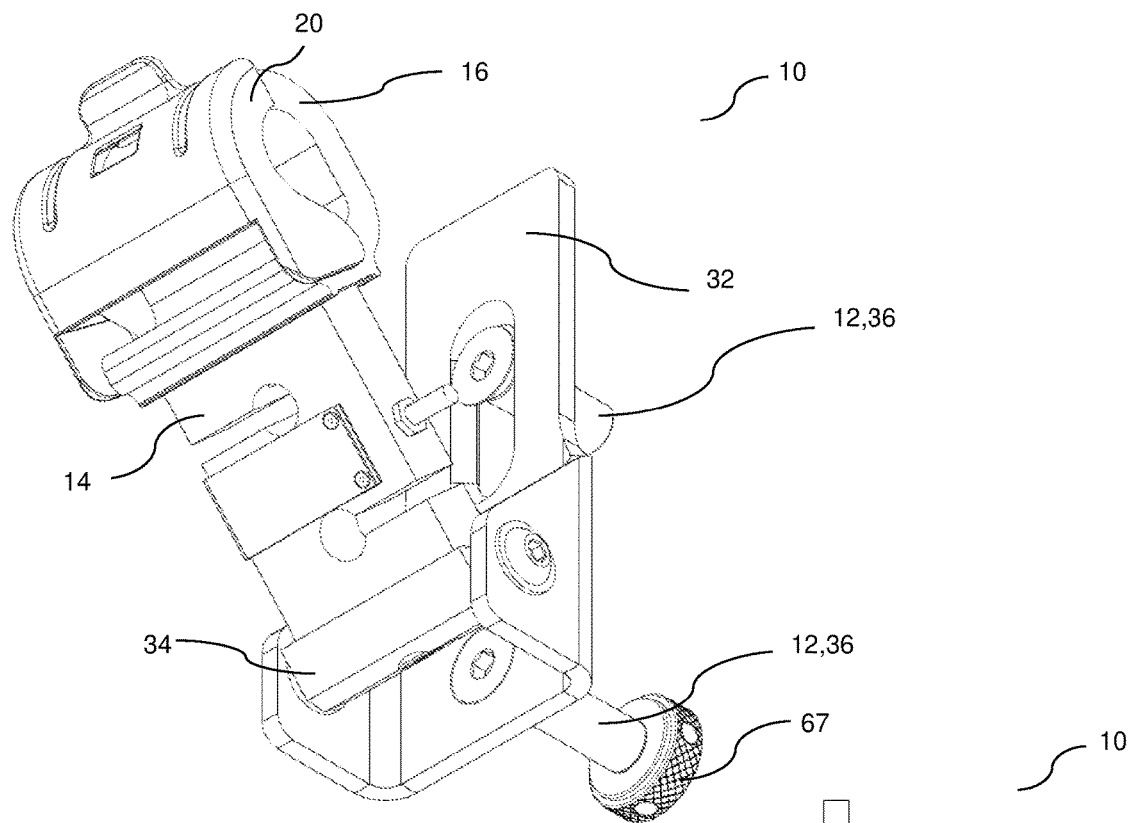
FIG. 9(a) is an isometric view of yet a further embodiment of an apparatus for measuring isometric muscle strength with the strain gauge angled outwardly.
FIG. 9(b) is a side view of the apparatus for measuring isometric muscle strength of FIG. 9(a) with the strain gauge angled outwardly.
Figure 9:
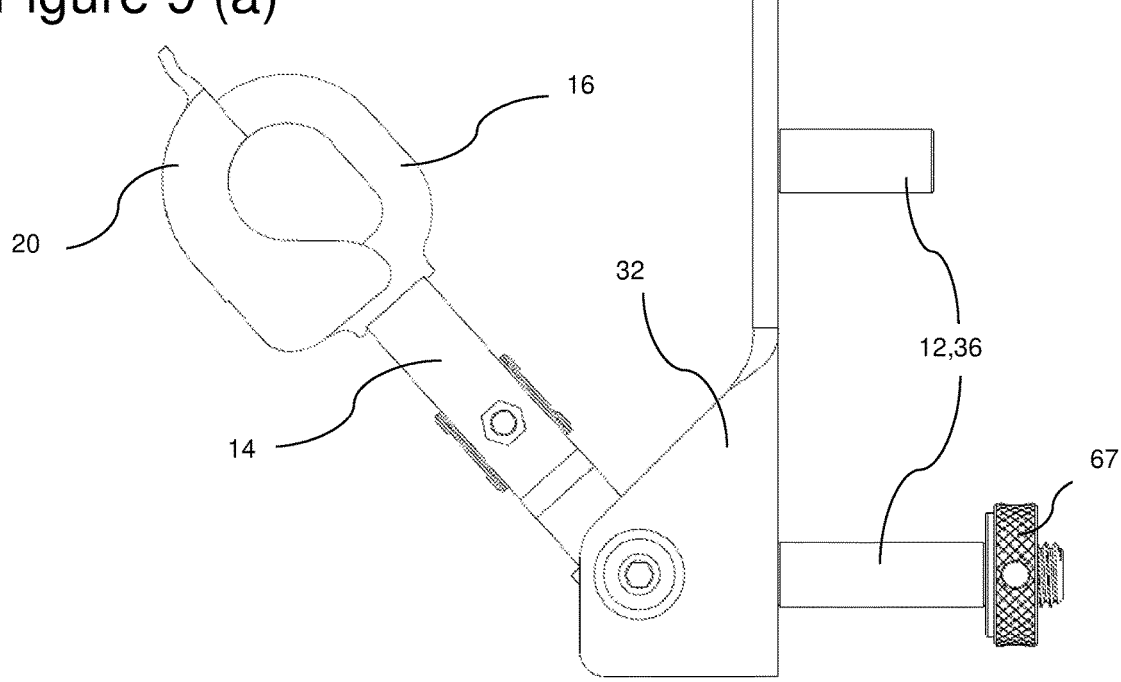
Figure 10:
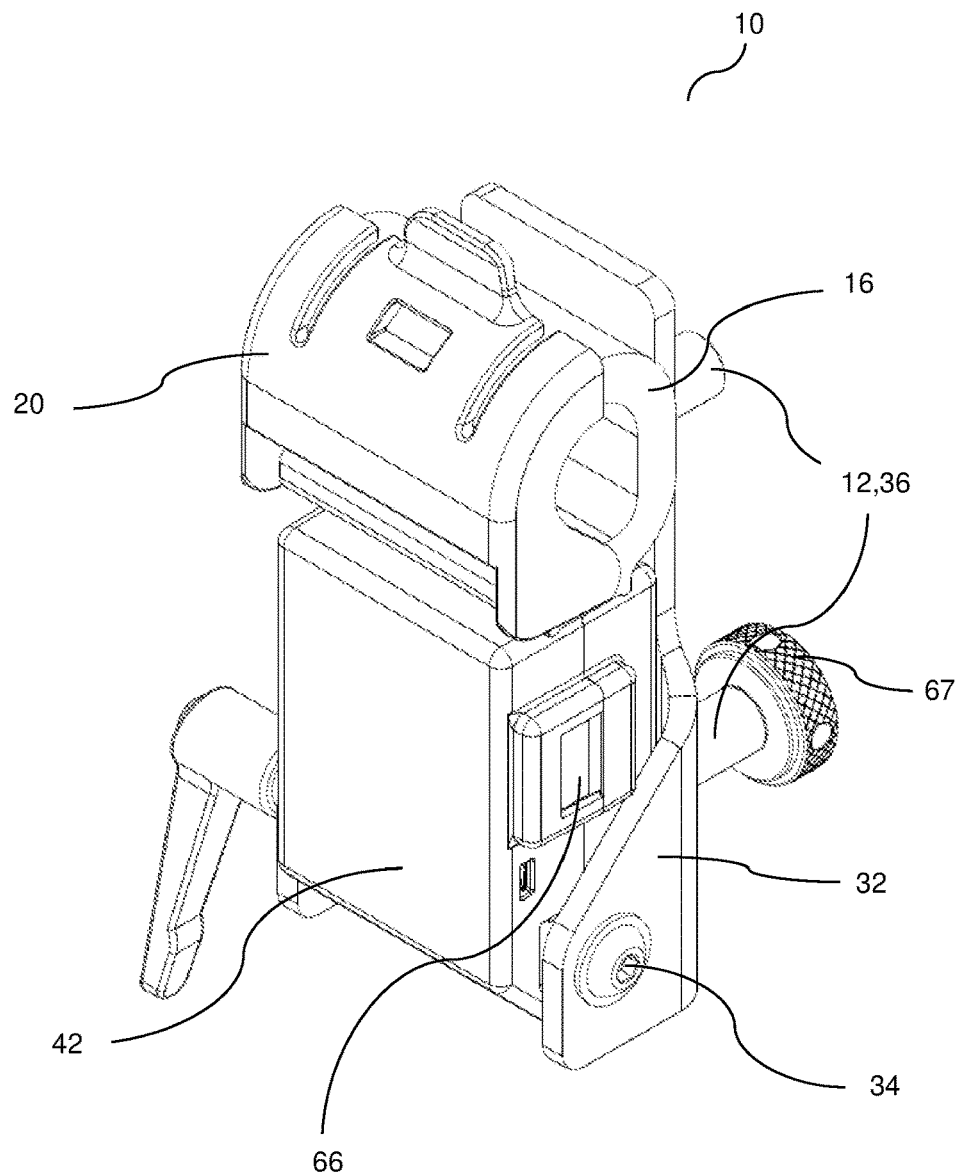
FIG. 10 is an isometric view of the apparatus for measuring isometric muscle strength of FIG. 9(a) with the strain gauge retracted.
Figure 11:
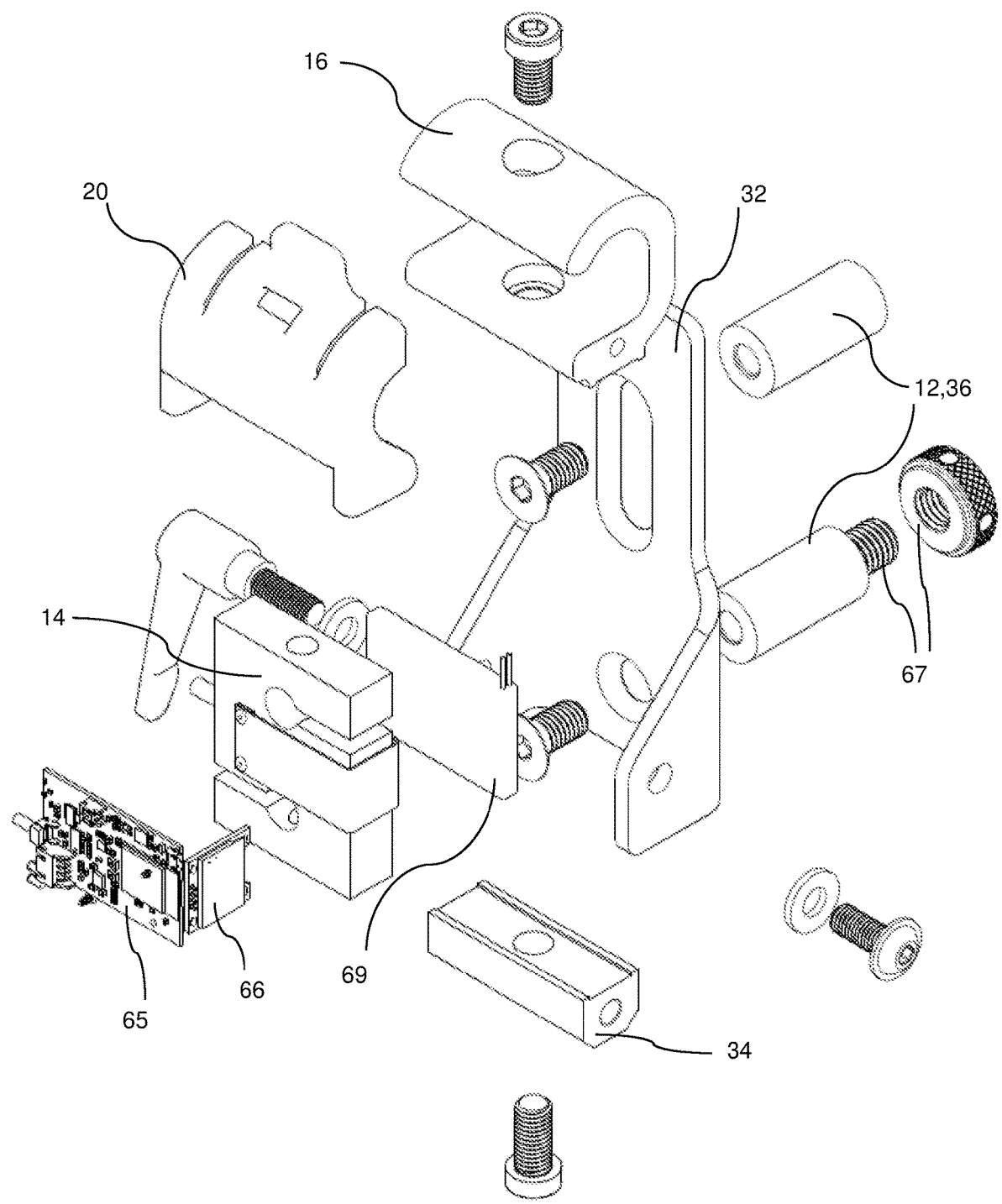
FIG. 11 is an exploded view of the apparatus of FIG. 10.
Figure 12:
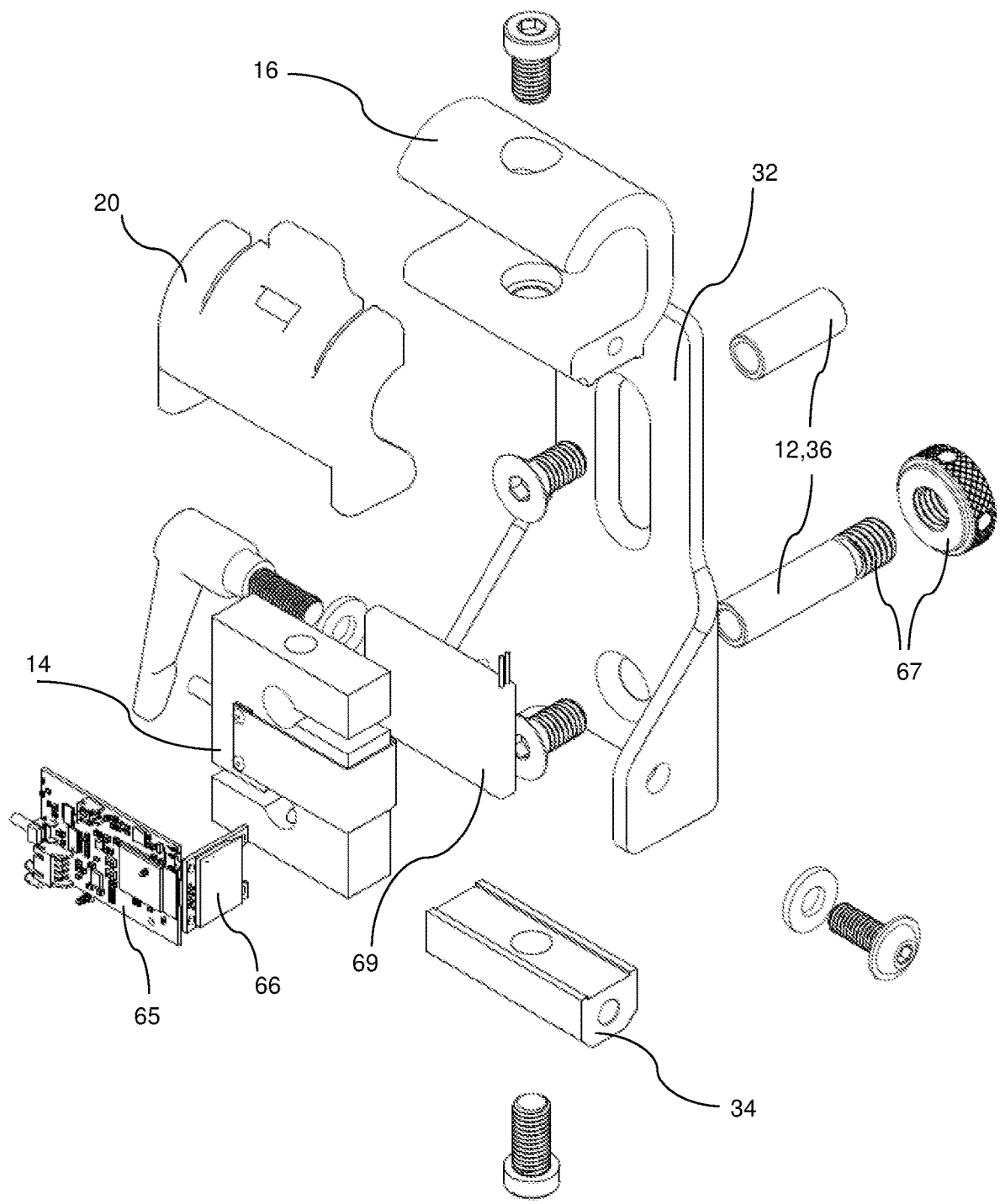
FIG. 12 is an exploded view of the apparatus of FIG. 10 with different sized pegs and bolts.
Figure 13:
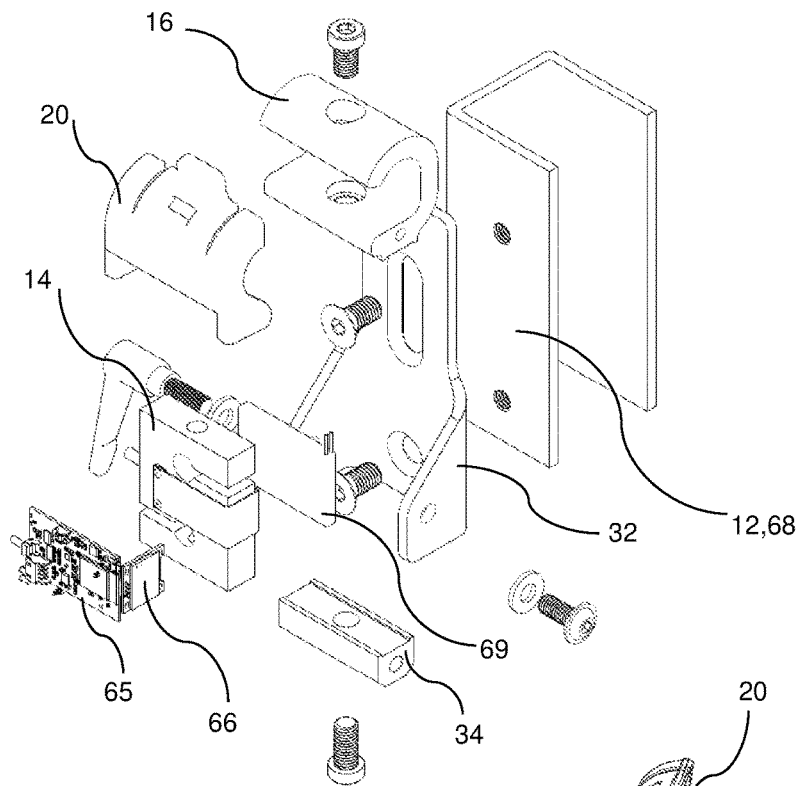
FIG. 13(a) is an exploded view of the apparatus of FIG. 10 with an adaptor for attachment to a manufacturer specific designed exercise equipment.
FIG. 13(b) is the view of FIG. 13(a) rotated 90 degrees.
Figure 13:
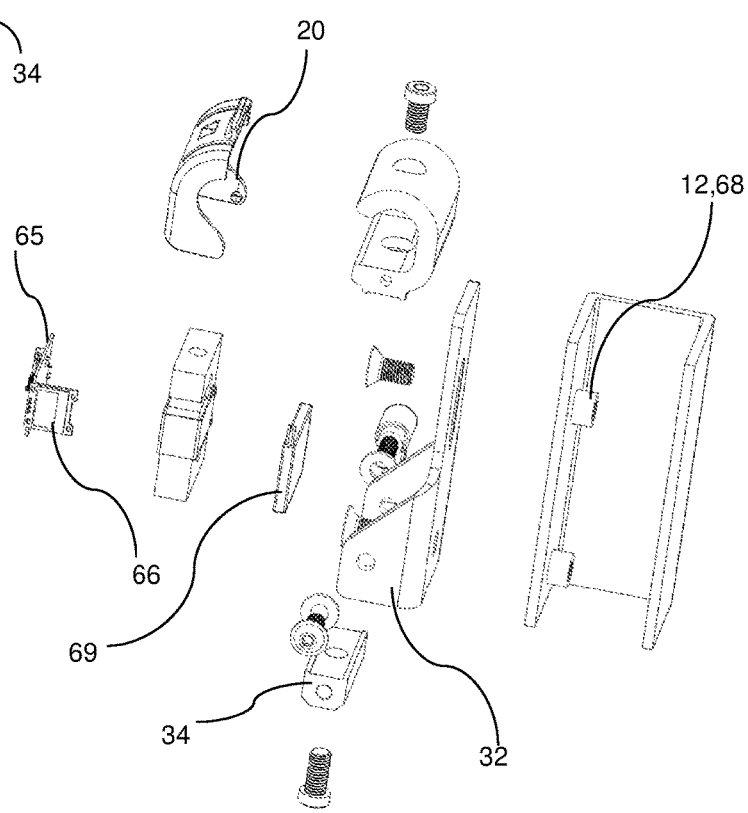

In use, the apparatus 10 may be attached to an item of exercise or weight training equipment in order to allow isostatic muscle strength of a person to be measured accurately. For example, FIG. 5 shows the apparatus 10 attached to an upright bar of a supporting frame of a barbell rack 48. The peg 36 that extends from the rear side of the apparatus 10 has been slotted into one of the apertures of the supporting frame that the bar holders of the rack are ordinarily attached to. The peg 36 provides that the apparatus 10 is removably secured to the support frame at a height that is convenient for use.

The clamping members 18, 20 are clamped around and to the elongate bar 50 of the barbell of the rack 48. The clamping members 18, 20 provide that the bar 50 is immovably connected to the apparatus 10 and, more particularly, immovably connected to the strain gauge 14 of the apparatus 10.

It will be understood that a further device identical to the apparatus 10 will be attached to a second upright bar of the supporting frame so that both ends of the barbell are secured to the supporting frame. For convenience, however, only the one apparatus 10 is shown in FIG. 5.

To measure the isometric muscle strength of a person, the user may try to lift the bar 50 which thereby causes an upwards force to be exerted on the bar 50. Because the bar 15 is fixed rigidly in position by the clamping members 18, 20, the muscles used by the user performing the lifting action are caused to contract isometrically. The lifting action causes the strain gauge 14 to be placed under tension which is measured by the strain gauge 14.

The forces measured by the strain gauge 14 may be retrieved from the apparatus 10 in real time. In the example in FIG. 5, the apparatus 10 comprises a communications port 52 disposed on the side of the strain gauge 14 that enables a peripheral device to be connected by wire to retrieve the force readings in real time. In other examples, the forces measured by the strain gauge 14 may be stored on a storage device housed in the control housing 42 and retrieved at a later date using the peripheral device. In other examples, the forces measured by the strain gauge 14 may be displayed on a screen 66 contained within housing 42.

The apparatus 10 advantageously provides a portable and convenient means for measuring isometric muscle strength. The attachment assembly 12, connection assembly 16 and strain gauge 14 are integrated into a single unit that may advantageously be attached to a wide variety of different exercise and weight training equipment with no modifications having to be made to the equipment.

The apparatus 10 may be used to measure isometric strength for rehabilitation purposes and for physio, sports, resistance training and weight training purposes.

The clamping members 18, 20 may be releasably attached to the apparatus 10 which enables them to be periodically removed and replaced with an alternative connection assembly 16. For example, FIGS. 6(a), 6(b), 7, 8(a) and 8(b) show the apparatus 10 with an alternative connection assembly 16 that may be used. The connection assembly 16 comprises an aperture 54 formed in a mounting plate attached to a top part of the strain gauge 14 that is configured to receive a strap member 56. This connection assembly 16 enables the strain gauge 14 to be connected to a component of exercise equipment that is pulled by a person in use.

For convenience, the strap member 56 has only been partially shown in the Figures. However, it will be understood that the strap member 56 as depicted may extend or be connected to a variety of different elongate strap assemblies commonly used in exercise equipment. For example, the strap member 56 may be connected to a long strap that extends vertically from the apparatus 10 up and over the frame of a weight training rack. When the end of the strap is pulled by a user, the pulling force causes the strain gauge 14 to be placed under tension which may then be measured by the strain gauge 14.

In other examples, the strap may extend outwardly from the apparatus 10 in a non vertical direction. For example, the strap may extend in a sideways direction relative to the apparatus 10 and be attached to a hand, foot or limb of the user. It is also possible that the direction that the strap is pulled in by the user may change during use. Because the strain gauge 14 is pivotally connected to the receptacle 32, if and when this happens the strain gauge 14 may advantageously pivot in response to the changes in direction. This ensures that the strain gauge 14 is always aligned with the direction of the pulling force. The apparatus 10 is, therefore, able to measure the pulling force exerted by the user on the strap accurately regardless of the direction that the strap is being pulled in.

In another example, two or more of the apparatuses 10 connected to straps may be attached to a structure to allow isometric muscle strength in different limbs of a person to be measured. For example, a pair of the apparatuses 10 may be connected to a weight training rack with the straps extending from the apparatuses 10 being secured to, respectively, the left and rights arms of a person such that differences in isometric strength in their arms can be measured.

The strain gauge 14 may also be configured to measure compressive forces exerted on the strain gauge 14. This enables the apparatus 10 to be attached to exercise equipment wherein pushing forces are exerted by the user to measure the isometric strength of the person applying such forces.

For the purpose of this specification, the word "comprising" means "including but not limited to", and the word "comprises" has a corresponding meaning.

The above embodiments have been described by way of example only and modifications are possible within the scope of the claims that follow.

The invention claimed is:

1. An apparatus for measuring isometric muscle strength and dynamic strength when a limb is fixed, the apparatus comprising:
an attachment assembly for releasably attaching the apparatus to a support frame of an item of exercise equipment; a strain gauge configured to measure compressive or tensional forces; and a connection assembly for releasably connecting the strain gauge to a moveable component of the exercise equipment such that forces exerted on the moveable component by isometric muscle contraction can be measured by the strain gauge, the connection assembly comprising first and second clamping members that are pivotable relative to one another for releasably clamping part of the strain gauge to the moveable component of the exercise equipment, the first clamping member attached to an end of the strain gauge and the second clamping member pivotally attached to the first clamping member.

2. The apparatus according to claim 1, wherein the connection assembly further comprises a latch for fastening the clamping members together when clamped around the moveable component.

3. The apparatus according to claim 2, wherein the latch comprises: a tab member connected to the first clamping member; and a slot formed in the second clamping member for receiving the tab member, wherein an end of the tab member comprises a flange for releasably securing the tab member in the slot when the clamping members are fastened together.

4. The apparatus according to claim 1, wherein:
the clamping members are configured to engage an elongate bar of a barbell rack; and each of the clamping members comprises a curved innermost surface for engaging a curved outermost surface of the elongate bar.

5. The apparatus according to claim 1, wherein the clamping members are releasably attached to the apparatus such that they may be removed and replaced with an alternative connection assembly.

6. The apparatus according to claim 1, wherein the apparatus further comprises a receptacle and the attachment assembly and strain gauge are each connected to the receptacle.

7. The apparatus according to claim 6, wherein a lowermost end of the strain gauge is attachable to the receptacle and an uppermost end of the strain gauge is attached to the connection assembly.

8. The apparatus according to claim 7, wherein the lowermost end of the strain gauge is pivotally attached to the receptacle such that the strain gauge may pivot relative to the receptacle in response to the moveable component of the exercise equipment being moved.

9. The apparatus according to claim 6, wherein the attachment assembly comprises an elongate peg that extends outwardly from the receptacle and is insertable into a hole of the support frame of the exercise equipment.

10. The apparatus according to claim 9, wherein the attachment assembly comprises a locking system for locking the elongate peg in the hole of the support frame once inserted therein.

11. The apparatus according to claim 10, wherein the locking system comprises at least one aperture formed in the elongate peg that is configured to receive a locking pin for locking the elongate peg in the hole of the support frame when inserted therein.

12. The apparatus according to claim 11, wherein the locking system comprises a plurality of apertures formed in the elongate peg for receiving the locking pin.

13. The apparatus according to claim 6, wherein the apparatus further comprises a rectangular control housing disposed between the strain gauge and the receptacle, wherein the control housing contains a processor and power source for operating the strain gauge.

14. The apparatus according to claim 1, wherein the strain gauge comprises a load cell configured such that an electrical resistance of the load cell changes in response to compressive or tensional forces exerted on the load cell.

15. The apparatus according to claim 14, wherein the load cell comprises an s-type load cell.

16. The apparatus according to claim 1, wherein the apparatus further comprises a communications port for connecting a peripheral device to the apparatus by wire for reading data measured using the strain gauge.

17. The apparatus according to claim 1, wherein the apparatus further comprises a radio transmitter for wirelessly reading data measured using the strain gauge using a peripheral device.

18. The apparatus according to claim 1, wherein the connection assembly comprises an aperture configured to receive a strap member for connecting the strain gauge to a moveable component of the exercise equipment that may be pulled by a user.

19. A system for measuring isometric muscle strength, the system comprising a plurality of apparatuses, wherein each of the apparatuses comprises the apparatus according to claim 1 wherein it is attached to a support frame of an item of exercise equipment.

20. The system according to claim 19, wherein:
the item of exercise equipment comprises a barbell rack; and the system comprises a pair of the apparatuses each attached to a support frame of the barbell rack.

21. The apparatus according to claim 13, further comprising a display in electrical communication with the control housing configured to display the forces measured by the strain gauge.

22. The apparatus according to claim 2, wherein:
the clamping members are configured to engage an elongate bar of a barbell rack; and each of the clamping members comprises a curved innermost surface for engaging a curved outermost surface of the elongate bar.

23. The apparatus according to claim 3, wherein:
the clamping members are configured to engage an elongate bar of a barbell rack; and each of the clamping members comprises a curved innermost surface for engaging a curved outermost surface of the elongate bar.

* * * * *